United States Patent
Park et al.

(10) Patent No.: US 7,592,475 B2
(45) Date of Patent: Sep. 22, 2009

(54) BRANCHED ALPHA-CYANOSTILBENE FLUOROPHORES

(75) Inventors: Sooyoung Park, Seoul (KR); Soonki Kwon, Kyeongsangnam-Do (KR); Byeongkwan An, Kyeongsangnam-Do (KR)

(73) Assignees: Dongwoo Fine-Chem Co., Ltd., Chullabuk-do (KR); Seoul National University Industry Foundation, Seoul (KR)

( * ) Notice: Subject to any disclaimer, the term of this patent is extended or adjusted under 35 U.S.C. 154(b) by 677 days.

(21) Appl. No.: 10/520,291

(22) PCT Filed: Jun. 29, 2002

(86) PCT No.: PCT/KR02/01245
§ 371 (c)(1), (2), (4) Date: Dec. 29, 2004

(87) PCT Pub. No.: WO2006/115306
PCT Pub. Date: Nov. 2, 2006

(65) Prior Publication Data
US 2007/0149799 A1  Jun. 28, 2007

(51) Int. Cl.
C07C 255/00  (2006.01)
C09K 11/06  (2006.01)
(52) U.S. Cl. .............. 558/401; 558/402; 252/301.16
(58) Field of Classification Search .............. 558/401, 558/402; 252/301.16
See application file for complete search history.

(56) References Cited

U.S. PATENT DOCUMENTS

| | | | |
|---|---|---|---|
| 4,047,948 A | 9/1977 | Horgan | |
| 4,536,457 A | 8/1985 | Tam | |
| 5,047,686 A | 9/1991 | Robertson | |
| 5,057,538 A | 10/1991 | Shiraishi et al. | |
| 6,338,910 B1 | 1/2002 | Ishibashi et al. | |
| 6,403,236 B1 | 6/2002 | Ohnishi et al. | |

FOREIGN PATENT DOCUMENTS

| | | |
|---|---|---|
| EP | 0 901 174 A2 | 3/1999 |
| EP | 0 985 719 A2 | 3/2000 |
| EP | 1 074 600 A2 | 2/2001 |
| JP | 01-117576 | 5/1989 |
| JP | 02-034681 | 2/1990 |
| JP | 04-308688 | 10/1992 |
| JP | 05-234661 | 9/1993 |
| JP | 05-239455 | 9/1993 |
| JP | 06-001972 | 1/1994 |
| JP | 06-032307 | 2/1994 |
| JP | 06-032307 B | 4/1994 |
| JP | 07-097355 | 4/1995 |
| JP | 07-126226 | 5/1995 |
| JP | 07-126615 | 5/1995 |
| JP | 07-331238 | 12/1995 |
| JP | 08-048656 | 2/1996 |
| JP | 08-087122 | 4/1996 |
| JP | 08-100172 | 4/1996 |
| JP | 08-259940 | 10/1996 |
| JP | 11-176576 | 7/1999 |
| JP | 2000-91077 A | 3/2000 |
| JP | 2001-123156 | 5/2001 |

OTHER PUBLICATIONS

Grovenstein et al., 1967, CAS: 67:43844.*
An et al., Journal of the American Chemical society, 2004, 126:10232-10233.*
J.-L. Brédas and A.J. Heeger, "Influence of Donor and Acceptor Substituents on the Electronic Characteristics of poly (paraphenylene vinylene) and poly (paraphertylene)," Chem. Phys. Lett., vol. 217, No. 5,6, pp. 507-512 (Jan. 28, 1994).
J.L. Segura, "The chemistry of electroluminescent organic materials," Acta Polymerica, vol. 49, Issue 7, pp. 319-344 (Jul. 1998).
Arno Kraft, Andrew C. Grimsdale, Andrew B. Holmes, "Electroluminescent Conjugated Polymers - Seeing Polymers in a New Light, "Angewandte Chemie International Edition, vol. 37, Issue 4, pp. 402-428 (1994).
Cesar Barbaro, et al., "Electrochemical Formulation of a Self-Doped Conductive Polymer in the Absence of a Supporting Electrolyte. The Copolymerization of o-Aminobenzenesulfonic Acid and Aniline," Advanced Materials, vol. 6, Issue 7-8, pp. 577-580 (1994).
Tetsuya Noda, et al., "A Novel Family of Amorphous Molecular Materials Containing an Oligothiophene Moiety as Color-Tunable Emitting Materials for Organic Electroluminscent Devices, "Advanced Materials, vol. 9, Issue 9, pp. 720-722 (1997).
Hiromatsu Tanaka, et al., "Novel hole-transporting materials based on triphyulamine for organic electroluminescent devices," Chem. Commun., pp. 2175-2176 (1996).
Chihaya Adachi, et al., "Electroluminescence in Organic Films with Three-Layer Structure," Japanese Journal of Applied Physics, vol. 27, No. 2, pp. L269-L271 (Feb. 1988).
Chihaya Adachi, et al., "Confinement of charge carriers and molecular excitons within 5-nm-thick emitter layer in organic electroluminescent devices with a double heterostructure," Appl. Phys. Lett., vol. 57, No. 6, pp. 531-533 (Aug. 6, 1990).
C.W. Tang, et al., "Electroluminescence of doped organic thin films," Journal of Applied Physics, vol. 65, No. 9, pp. 3610-3616 (May 1, 1989).
PCT International Preliminary Examination Report for PCT/KR2002/001245, 5 pgs. (Oct. 30, 2004).
PCT International Search Report for PCT/KR2002/01245, 3 pgs. (Mar. 27, 2003).

* cited by examiner

*Primary Examiner*—Rei-tsang Shiao
(74) *Attorney, Agent, or Firm*—Blakely, Sokoloff, Taylor & Zafman LLP

(57) ABSTRACT

A branched α-cyanostilbene fluorescent materials with a new structure useful to the organic electroluminescence display (OELD), which includes the organic substance in the state of powder, liquid and film with the stilbene core structure and the terminal branched phenyl structure.

The fluorescent materials of the invention exhibits the high luminescent efficiency and is capable of tuning the fluorescent colors of red, green and blue according to the core structure in the molecular, i.e., the structure of stilbene radical, particularly it exhibits the higher luminescent efficiency in the state of solid more than solution.

3 Claims, 4 Drawing Sheets

BRANCHED ALPHA-CYANOSTILBENE FLUOROPHORES

CROSS-REFERENCE TO OTHER APPLICATIONS

This application is a 371 PCT/KR02/01245 filed on Jun. 29, 2002.

TECHNICAL FIELD

The present invention relates to novel branched fluorescent materials having a α-cyanostilbene core structure, which can variously tune the fluorescent colors of red, green and blue.

BACKGROUND ART

Recently, the organic EL element has been attracted considerable attention as a most suitable material for the flat panel display (FPD) having high brightness. Under this trend, a lot of the researches and developments have been carried out vigorously. The organic EL element has a structure wherein the luminescent layer is inserted between the two electrodes. The hole streaming in the anode positively charged recombines with the electron flowing in from the cathode negatively charged in the luminescent layer to become finally luminescent. The both materials of high molecular and low molecular can all be utilized to the production of the organic EL element. The both of them are proved to provide the organic EL element having high brightness.

The organic EL element is divided broadly into the two types. The one forms the luminescent layer by the use of the materials comprising the fluorescence dye to transporting the charges (See Journal of the Applied Physics, 65, 3610, 1989). The other utilizes the luminescence dye per se as the luminescent layer (See Japanese Journal of the Applied Physics, 27, L269, 1988).

The organic EL element utilizing the luminescence dye per se as the luminescent layer is further divided into the following three types. The first one is the three layers element wherein the luminescent layer is inserted between the hole transporting layer and the electron transporting layer, the second one is the two layers element wherein the hole transporting layer and the luminescent layer are laminated to the other one, and the third one is the two layers element wherein the electron transporting layer and the luminescent layer are laminated to the other one. So, the organic EL element has been known as exhibiting the improved luminescence efficiency in case that it consists of two or three layers.

In said organic EL element, the electron transporting layer comprises an electron transporting compound to function as transporting the electron from the cathode to the luminescent layer. Both of the hole injection layer and the hole transporting layer comprise the hole transporting substance to function as transporting the hole from the anode to the luminescent layer. When the hole injection layer is inserted between the anode and the luminescent layer, a number of increased holes can be flowed into the luminescent layer from the low electric field and the electrons streamed in from the cathode or the electron injection layer can be preserved restrictedly in the luminescent layer. Accordingly, the luminescent efficiency can be improved and thus the organic EL element with an excellent efficiency of the luminescence can be realized.

The various kinds of materials concentrated on triphenylamine derivatives used usually have been known widely as the materials used for such organic EL element. However, only very small number of materials are suitable for the practical use. N,N'-diphenyl-N,N'di(3-methylphenyl)-4,4'-diaminophenyl(TPD), for instance, has been informed (Applied Physics Letter, Vol. 57, No. 6, 531, 1990). However, this compound is thermally unstable and has a problem in respect to the life of element produced. Though lots of triphenylamine derivatives have been known (U.S. Pat. Nos. 5,047,686, 4,047,948 and 4,536,457, Japanese Patent Document No. 06-32307 and Japanese Laid Open Patent Application Nos. 05-234681, 5-239455, 8-87122 and 8-259940), the most of them are not satisfactory at the aspect of the feature.

Neither the star-burst amine derivatives disclosed either in Japanese Laid Open Patent Application No. 4-308688 or 6-1972, or in the literature of Advanced Material, Vol. 6, 577, 1994 satisfy neither the essential requirement for the organic EL element, i.e., the high luminous efficiency and the long life, nor satisfy it the respective compounds disclosed in Japanese Laid Open Patent Application Nos. 7-126226, 7-126615, 7-331238, 7-97355, 8-48656 and 8-100172 and the literature of Journal of the Chemical Society Chemical Communication, p2175, 1996.

The compound having thiophene-ring disclosed in the literature of Advanced Material Vol. 9, 720, 1997 has a defect to emit the long wavelength beam.

As set forth hereinabove, the materials used for the usual organic EL element has still been required the improved efficiency. Accordingly, an excellent material capable of improving the luminous efficiency has been desired.

SUMMARY OF THE INVENTION

Under those circumstances, the inventors made an attempt to solve the problems in respect to the usual organic EL element and to render a new efficacy, and then synthesized a novel branched stilbene compound, whereby the inventors have discovered that the efficiency required for the organic EL element can be realized at last and possibly completed the present invention.

Accordingly, the object of the invention is directed to provide a new material with the organic fluorescent materials.

An other object of the invention is to provide a new material with the organic fluorescent materials, which can tune the fluorescent colors of red, green and blue.

DETAILED DESCRIPTION OF THE INVENTION

The invention is explained in detail herein below.

The branched α-cyanostilbene derivatives of the invention are polyphenyl derivatives of the formula 1, which can be prepared by the method showing in Examples 1 to 13.

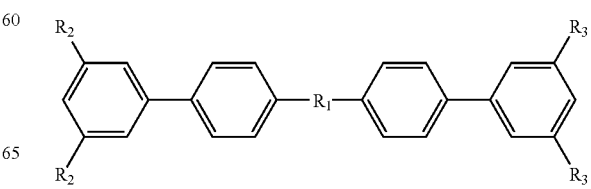

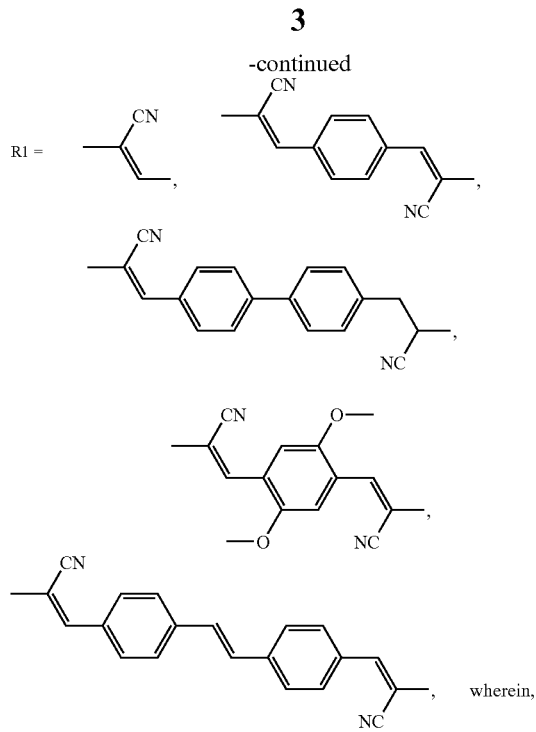

wherein, $R_2$ and $R_3$ denotes respectively $C_1$-$C_6$ alkyl, $C_1$-$C_6$ alkoxy, substituted or unsubstituted amino, substituted or unsubstituted aryl, or substituted or unsubstituted heterocycle, and the substituted or unsubstituted aryl, or substituted or unsubstituted heterocycle can be condensed at the optional site of the corresponding two benzene rings.

The branched α-cyanostilbene derivatives of the formula 1 of the invention are used in the composition in the amount of 1 to 99% by weight based on the total weight of the organic electro-luminescent composition.

On the other hand, the branched stilbene fluorescent materials produced show the ultraviolet ray absorption appeared in FIG. 1 and exhibit the fluorescent emission feature shown in FIG. 2 and the electro-luminescent feature shown in FIG. 3. Particularly, all the luminescent colors of the materials in the present invention are emitted throughout the whole color area (red, green, blue) to change the core structure in the branched basic structure. Accordingly, the present invention is considered as an invention capable of color tuning.

Further, most materials of the invention display the early decomposition temperature of 350 to 400° C. as shown in FIG. 4 to exert the high thermal stability.

EXAMPLES

Figure 1:
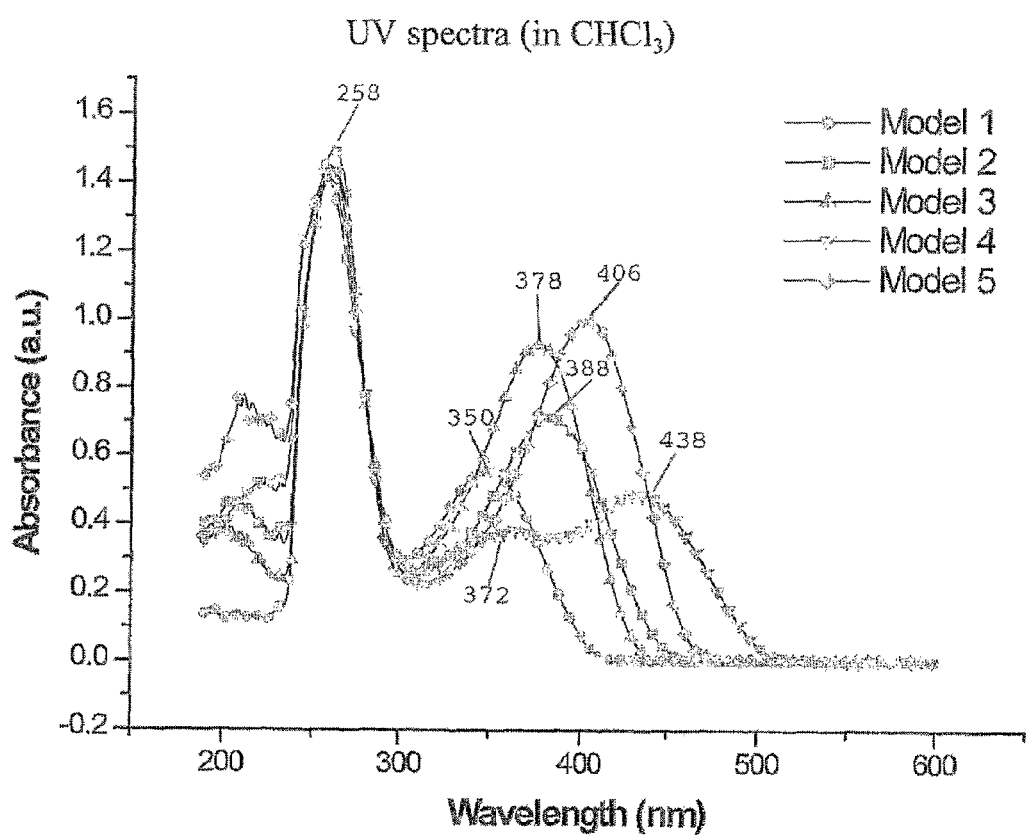
FIG. 1 is a diagram showing the ultraviolet absorption spectrum of the synthesized organic fluorescent materials.
Figure 2:
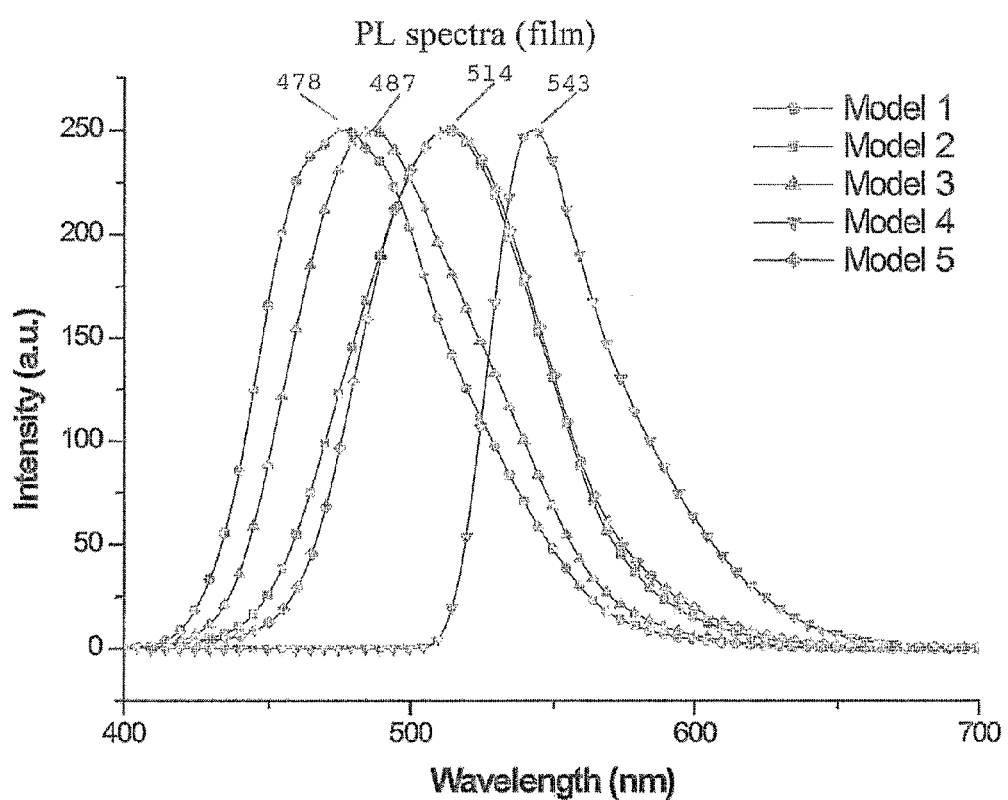
FIG. 2 is a diagram showing the fluorescent emission spectrum of the synthesized organic fluorescent materials in the solid state.
Figure 3:
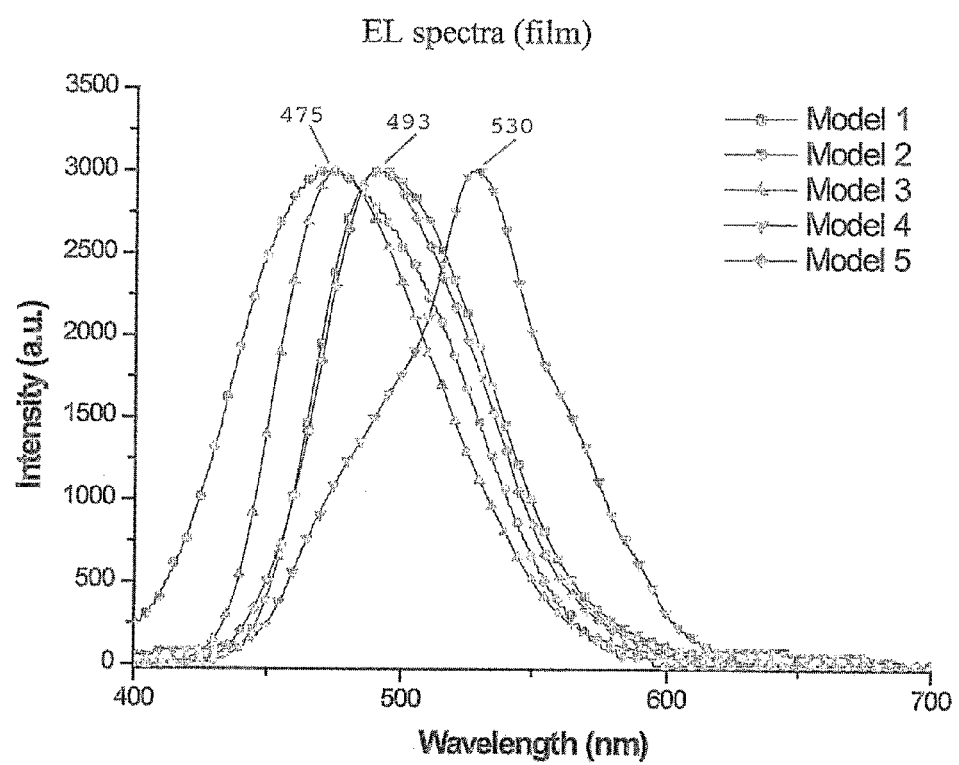
FIG. 3 is a diagram showing the electro-luminescent spectrum of the synthesized organic fluorescent materials in the solid state.
Figure 4:
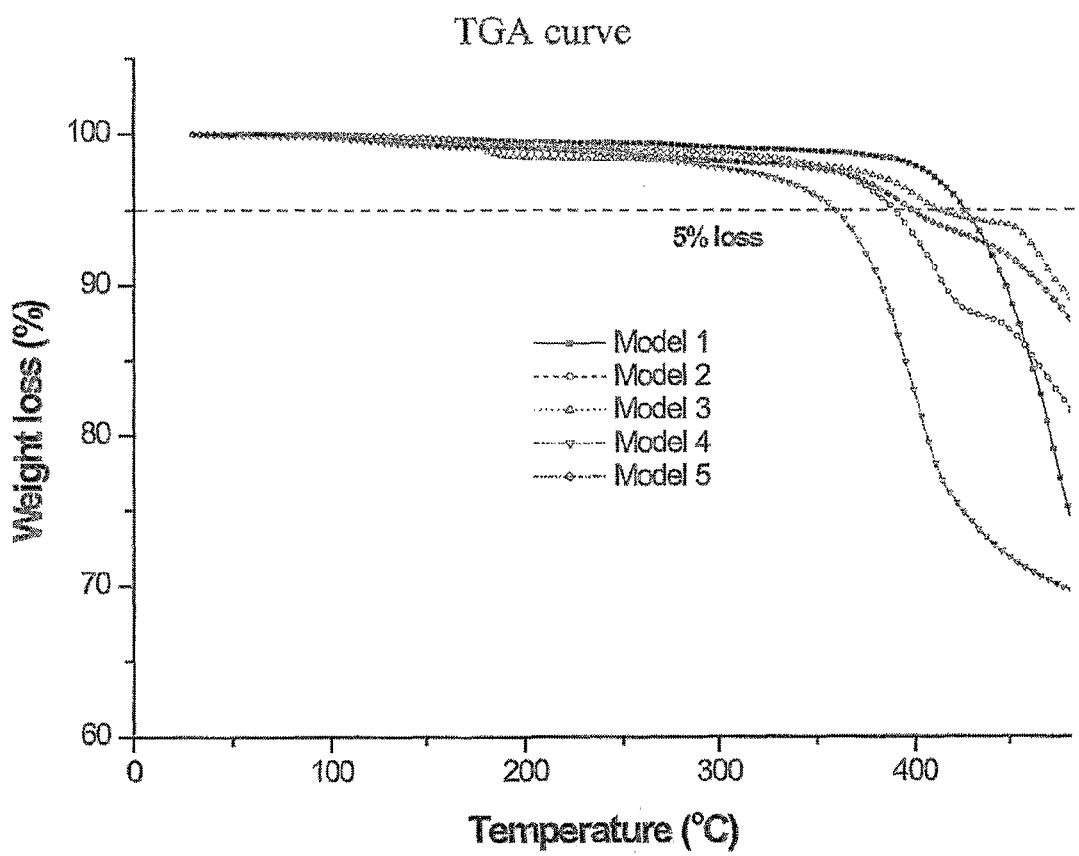
FIG. 4 is a diagram indicating the result of the thermo-gravimetry analysis (TGA) of the organic fluorescent materials synthesized.
Figure 5:
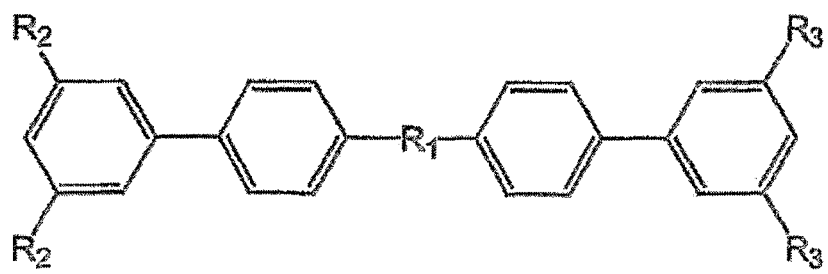
FIG. 5 is a scheme presenting the basic structure of the new branched α-cyanostilbene organic fluorescent materials exhibiting the luminescent feature.

The present invention will be understood more readily with reference to the following examples, however, those examples are not to be construed to limit the scope of the invention. The modification and application thereof usually acceptable in the pertinent art fall within the scope of the invention.

The process for producing branched α-cyanostilbene derivatives of formula 1 is explained herein below.

Examples 1 to 8

Preparation of a Compound for Producing Branched α-cyanostilbene Derivatives of Formula 1

Example 1

Preparation of 4,4'-dimethylbiphenyl

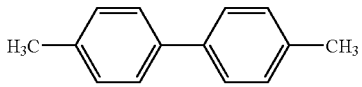

10 g(79 mmol) of 4-chlorotoluene was added into the solution of purified dimethylformamide together with 0.51 g(3.9 mmol) of nickel chloride(II), 0.617 g(3.9 mmol) of 2,2'-bipyridine, 4.14 g(15.7 mmol) of triphenylphosphine and 122.3 mmol of zinc to be agitated at 90° C. for 5 hours. When the reaction was completed, the reaction mix was poured in 1N aqueous solution of hydrogen chloride to break the complex structure. The reactant was extracted with methylene chloride and the solvent was distilled off under reduced pressure. The resulted product was washed around twice with methanol and suction-filtrated to dryness. Yield; 75%.

$^1$H-NMR(CDCl$_3$, ppm): 7.49(d, 4H, Ar—H), 7.25(d, 4H, Ar—H), 2.38(s, 6H, —CH$_3$). IR(KBr, cm$^{-1}$): 3040, 2900, 1500, 1110, 800. MS (EI) (Calculated for C$_{14}$H$_{14}$, 182.26; Found, 182).

Example 2

Preparation of 4'-methylbiphenyl-4-carboaldehyde

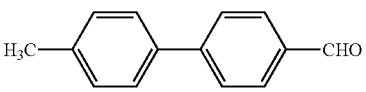

Into CCl$_4$ solvent, 2.4 g(13.3 mmol) of the compound produced in Example 1 (Compound 1) and 0.536 g(3.0 mmol) of N-bromosuccinimide were added and refluxed for 24 hours. After cooled down, the reactant was suction-filtrated and the resultant solution was washed with distilled water and then was dried with anhydrous magnesium sulfate. The dried product was dissolved again in chloroform together with 5.34 g(51.2 mmol) of hexamethylenetetraamine and refluxed for 5 hours. After the reactant was cooled down, the solvent was distilled off under reduced pressure and the residue was refluxed severely in acetic acid/H$_2$O(17 mL/17 mL) at 120° C. for 2 hours. Finally, 7 mL of HCl was added to be refluxed. After cooled down, the reactant was extracted with methylene chloride. The solution was distilled off under reduced pressure and the residue was purified through the column chromatography (silica gel, ethyl acetate/n-hexane=1:3) to be dried. Yield; 24%.

$^1$H-NMR(CDCl$_3$): 10.0(s, 1H, —CHO), 7.95(d, 2H, Ar—H), 7.75(d, 2H, Ar—H), 7.55(d, 2H, Ar—H), 7.28(d, 2H, Ar—H), 2.42(s, 3H, —CH$_3$).

Example 3

Preparation of 1,3,5-tris(4-methyl-phenyl)-benzene

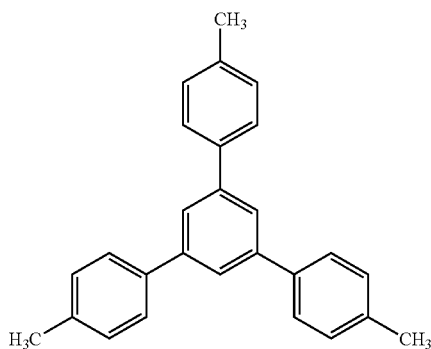

20 g(149.1 mmol) of 4-methylacetophenone was added to ethanol and agitated at low temperature (5-10° C.) while introducing gradually 17.08 mL(149.1 mmol) of SiCl$_4$ through a syringe. After the agitation for 24 hours, the product was suction-filtrated. The resulted solid product was washed several times with ethanol and then was dried under a vacuum. Yield; 82%.

$^1$H-NMR(CDCl$_3$, ppm): 7.72(s, 3H, Ar—H), 7.60(d, 6H, Ar—H), 7.29(d, 6H, Ar—H), 2.41(s, 9H, —CH$_3$). IR(KBr, cm$^{-1}$): 3010, 2950, 1600, 1500, 1410, 1390, 800. MS (EI) (Calculated for C$_{27}$H$_{24}$, 348.38; Found, 348).

Example 4

Preparation of [1,3-bis(4-methyl-phenyl)-5-(4-cyanomethyl-phenyl)]-benzene

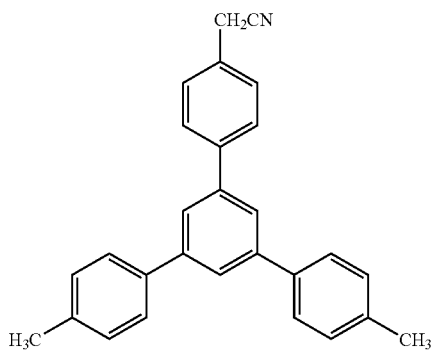

5 g(14.4 mmol) of the compound produced in Example 3 (Compound 4) and 2.56 g(14.4 mmol) of N-bromosuccinimide were added in CCl$_4$ solvent and refluxed for 24 hours. The reactant was cooled down and suction-filtrated. The filtrate was washed with distilled water and dried with anhydrous magnesium sulfate. The solvent was distilled off under reduced pressure. The resulted product was dissolved again in THF and the solution was mixed with ethanol wherein 2.35 g(48 mmol) of NaCN was dissolved to be agitated for 5 hours. After the completion of the reaction, the solvent was distilled off under reduced pressure and the residue was washed with water to be extracted with methylene chloride. The solution was distilled off under reduced pressure and the residue was purified through the column chromatography (silica gel, ethyl acetate/n-hexane=1:3) to be dried. Yield; 39% (Compound 5 was obtained as the byproduct. Yield; 17%).

$^1$H-NMR(CDCl$_3$, ppm): 7.76(s, 1H, Ar—H), 7.72(d, 4H, Ar—H), 7.60(d, 4H, Ar—H), 7.45(d, 2H, Ar—H), 7.30(d, 4H, Ar—H), 3.81(s, 2H, —CH$_2$CN), 2.46(s, 6H, (—CH$_3$)$_2$). IR(KBr, cm$^{-1}$): 3010, 2950, 2250, 1600, 1500, 1410, 800. MS (EI) (Calculated for C$_{28}$H$_{23}$N, 373.49; Found, 373).

Example 5

Preparation of [1,3-bis(4-methyl-phenyl)-5-(4-formyl)-phenyl]-benzene

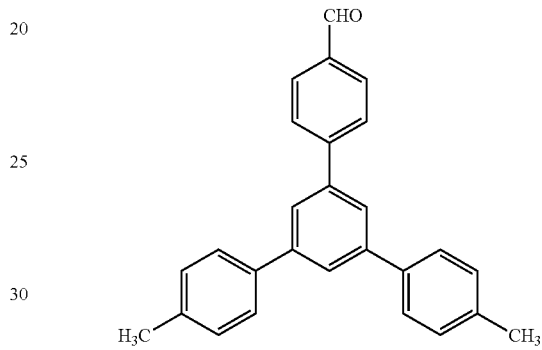

4.67 g(13.4 mmol) of the compound 4 and 3.58 g(20.0 mmol) of N-bromosuccinimide were added in CCl$_4$ solvent and refluxed for 24 hours. The reactant was cooled down and suction-filtrated. The filtrate was washed with distilled water and dried with anhydrous magnesium sulfate. The solvent was distilled off under reduced pressure. The residue was purified through the column chromatography (silica gel, ethyl acetate/n-hexane=1:5) to be dried. The resulted product was dissolved again in chloroform together with 4.4 g(42.7 mmol) of hexamethylenetetraamine and the solution was refluxed for 5 hours. After the reactant was cooled down, the solvent was distilled off under reduced pressure and the residue was refluxed intensely in acetic acid/H$_2$O(25 mL/25 mL) at 120° C. for 2 hours. Finally, 10 mL of HCl was added to be refluxed. After cooled down, the reactant was extracted with methylene chloride. The solution was distilled off under reduced pressure and the residue was purified through the column chromatography (silica gel, ethyl acetate/ n-hexane=1:3) to be dried. Yield; 17%.

$^1$H-NMR(CDCl$_3$, ppm): 10.0(s, 1H, —CHO), 8.0(d, 2H, Ar—H), 7.87-7.77(m, 5H, Ar—H), 7.60(d, 4H, Ar—H), 7.28 (d, 4H, Ar—H), 2.42(s, 6H, (—CH$_3$)$_2$).

Example 6

Preparation of Biphenyl-4,4'-dicarboaldehyde

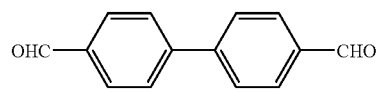

2.5 g(13.7 mmol) of the compound 1 and 6.1 g(34.3 mmol) of N-bromosuccinimide were added in CCl$_4$ solvent and refluxed for 24 hours. The reactant was cooled down and suction-filtrated. The filtrate was washed with distilled water and dried with anhydrous magnesium sulfate. The resulted product was dissolved again in chloroform together with 6.6 g(47.1 mmol) of hexamethylenetetraamine and the solution was refluxed for 5 hours. After the reactant was cooled down, the solvent was distilled off under reduced pressure and the residue was refluxed intensely in acetic acid/H$_2$O(17 mL/17 mL) at 120° C. for 2 hours. Finally, 7 mL of HCl was added to be refluxed. After cooled down, the reactant was extracted with methylene chloride. The solution was distilled off under reduced pressure and the residue was purified through the column chromatography (silica gel, ethyl acetate/n-hexane=1:3) to be dried. Yield; 69%.

$^1$H-NMR(CDCl$_3$): 10.1(s, 2H, —CHO), 7.99(d, 4H, Ar—H), 7.79(d, 4H, Ar—H).

Example 7

Preparation of 4,4'-dimethyl-stilbene

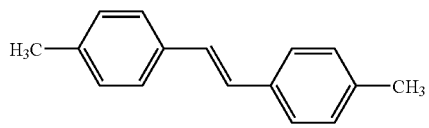

2.4 g(5.37 mmol) of (4-methylbenzyl)triphenylphosphonium bromide and 0.98 g(60%, 24.4 mmol) of NaH were refluxed in toluene for 6 hours. After cooled down, 0.586 g(4.88 mmol) of 4-methylbenzaldehyde was introduced gradually to the solution to be refluxed again for 6 hours. The resulted product was treated with water to be extracted with ethyl acetate. The solvent was distilled off and the residue was recrystallized in ethanol. Yield; 71%.

$^1$H-NMR(CDCl$_3$): 7.64(d, 4H, Ar—H), 7.16(d, 4H, Ar—H), 6.90(s, 2H, vinyl).

Example 8

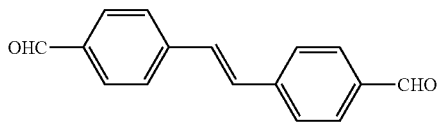

Preparation of 4,4'-diformyl-stilbene

Into CCl$_4$ solvent, 2 g(9.6 mmol) of the compound produced in Example 7 (Compound 9) and 4.27 g(24.0 mmol) of N-bromosuccinimide were added and refluxed for 24 hours. After cooled down, the reactant was suction-filtrated and the resultant solution was washed with distilled water and then was dried with anhydrous magnesium sulfate. The dried product was dissolved again in chloroform together with 4.0 g(38.4 mmol) of hexamethylenetetraamine and refluxed for 5 hours. After the reactant was cooled down, the solvent was distilled off under reduced pressure and the residue was refluxed severely in acetic acid/H$_2$O(17 mL/17 mL) at 120° C. for 2 hours. Finally, 7 mL of HCl was added to be refluxed. After cooled down, the reactant was extracted with methylene chloride. The solution was distilled off under reduced pressure and the residue was purified through the column chromatography (silica gel, ethyl acetate/n-hexane=1:3) to be dried. Yield; 20%.

$^1$H-NMR(CDCl$_3$): 10.03(s, 2H), 7.92(d, 4H, Ar—H), 7.71(d, 4H, Ar—H), 7.30(s, 2H, vinyl).

Examples 9 to 13

Preparation of Branched α-cyanostilbene Derivatives of Formula 1

Example 9

Preparation of 2,3-bis-[3,5-(4-methyl-phenyl)-biphenyl-4-yl]-acrylonitrile (Model 1)

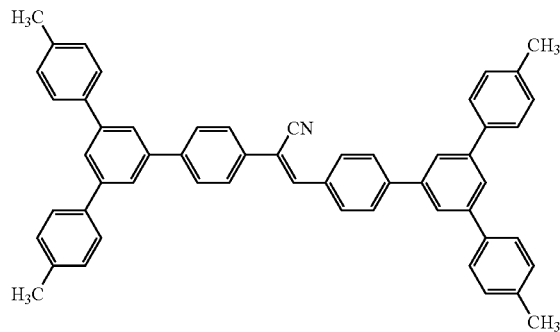

Model 1

0.31 g(0.8 mmol) of the compound produced in Example 4 (Compound 5) and 0.2 g(0.8 mmol) of the compound produced in Example 5 (Compound 6) were dissolved in tert-butylalcohol and purified THF solvent at 50° C. and 0.08 mL of tetrabutylammoniumhydroxide (1M solution in methanol) was gradually introduced to the solution to be agitated at 50° C. for 20 minutes. The precipitate was suction-filtered to be dried. Yield; 93%.

$^1$H-NMR(CDCl$_3$, ppm): 8.06(d, 2H, Ar—H), 7.80(m, 12H, Ar—H), 7.66(s, 1H, vinyl proton), 7.62(d, 8H, Ar—H), 7.32(d, 8H, Ar—H), 2.43(s, 12H, —CH$_3$). IR(KBr, cm$^{-1}$): 3040, 2950, 2230, 1600, 1510, 800. MS (EI) (Calculated for C$_{55}$H$_{43}$N, 717.94; Found, 718).

Example 10

Preparation of Model 2

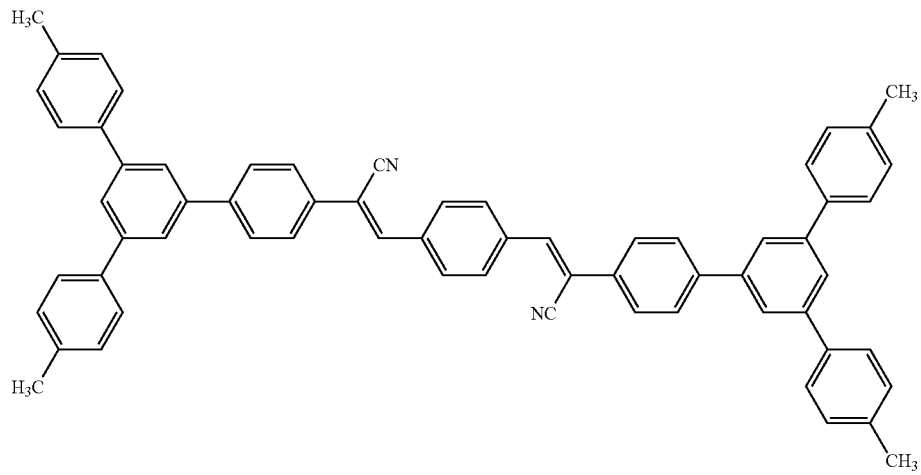

Model 2

The same synthesizing method of Knoevenage 1 as the method for Model 1 was carried out. Yield; 74%.

$^1$H-NMR(CDCl$_3$, ppm): 8.06(s, 4H, Ar—H), 7.80(m, 14H, Ar—H), 7.64(m, 10H, Ar—H), 7.30(d, 8H, Ar—H), 2.43(s, 12H, —CH$_3$). IR(KBr, cm$^{-1}$): 3040, 2950, 2222, 1600, 1500, 1280, 800, 750. MS (EI) (Calculated for C$_{55}$H$_{43}$N, 845.08; Found, 845).

Example 11

Preparation of Model 3

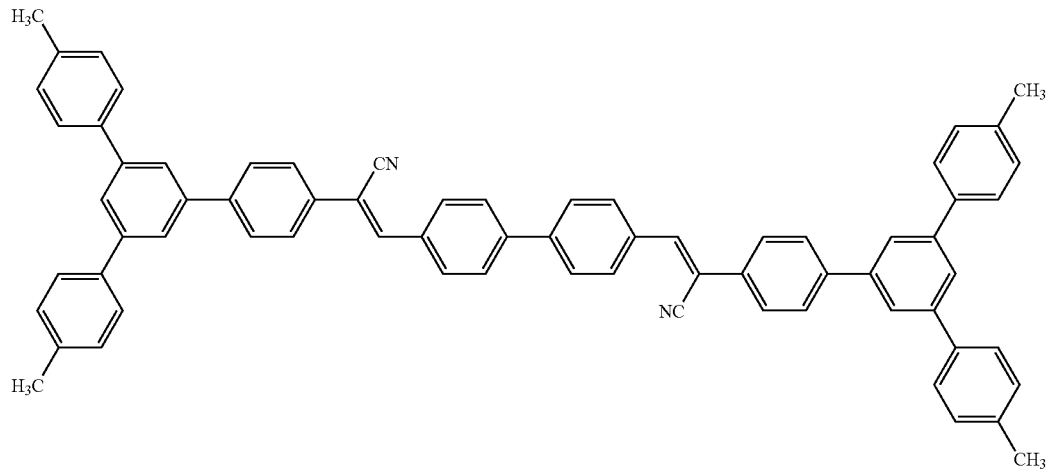

Model 3

The same synthesizing method of Knoevenage 1 as the method for Model 1 was carried out. Yield; 97%.

$^1$H-NMR(CDCl$_3$, ppm): 8.06(d, 4H, Ar—H), 7.85(m, 18H, Ar—H), 7.66(m, 10H, Ar—H), 7.62(d, 8H, Ar—H), 2.43(s, 12H, —CH$_3$). IR(KBr, cm$^{-1}$): 3040, 2950, 2222, 1600, 1500, 1280, 810, 750. MS (EI) (Calculated for C$_{55}$H$_{43}$N, 921.18; Found, 921).

Example 12

Preparation of Model 4

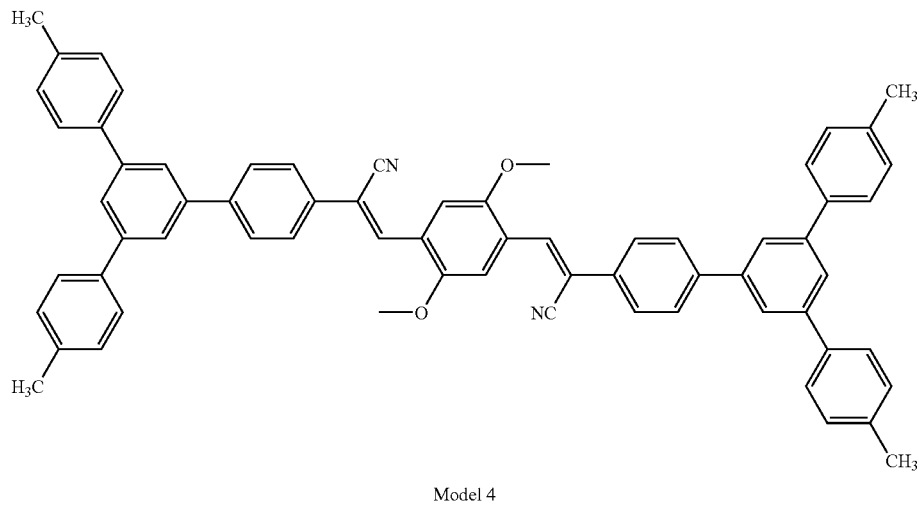

Model 4

The same synthesizing method of Knoevenage 1 as the method for Model 1 was carried out. Yield; 83%.

$^1$H-NMR(CDCl$_3$, ppm): 8.10(s, 1H, Ar—H), 7.96(s, 1H, Ar—H), 7.80(m, 14H, Ar—H), 7.62(m, 10H, Ar—H), 7.26 (d, 8H, Ar—H), 4.00(s, 6H, —OCH$_3$), 2.43(s, 12H, —CH$_3$). IR(KBr, cm$^{-1}$): 3040, 2950, 2220, 1600, 1510, 1230, 800, 750. MS (EI) (Calculated for C$_{55}$H$_{43}$N, 905.13; Found, 905).

Example 13

Preparation of Model 5

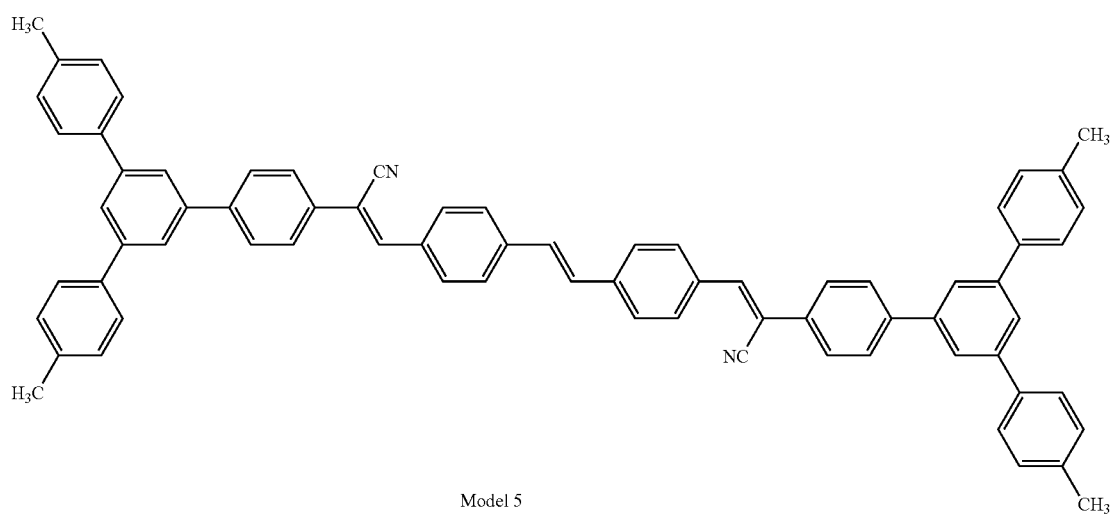

Model 5

The same synthesizing method of Knoevenage 1 as the method for Model 1 was carried out. Yield; 93%.

$^1$H-NMR(CDCl$_3$, ppm): 7.98(d, 4H, Ar—H), 7.78(m, 14H, Ar—H), 7.62(m, 15H, Ar—H), 7.32(d, 9H, Ar—H), 2.43(s, 12H, —CH$_3$). IR(KBr, cm$^{-1}$): 3040, 2950, 2222, 1600, 1500, 1380, 800, 750. MS (EI) (Calculated for C$_{55}$H$_{43}$N, 947.21; Found, 947).

INDUSTRIAL APPLICABILITY

The branched α-cyanostilbene fluorescent materials with a new structure of the formula 1 of the present invention can be called an organic electro-luminescent material greatly useful to the production of the organic EL element, which exhibit the luminescent feature in all the state of powder, liquid and film.

Particularly, it is the initiative substance which can regulate the colors of red, green and blue by means of changing the core structure such as the substituent RI and can produce the high efficient display device capable of the whole color display. Furthermore, all the said materials exhibit the excellent heat stability and thus exert the excellent stability in the manufacturing process of the organic EL element.

What is claimed is:

1. α-cyanostilbene compounds of the formula 1:

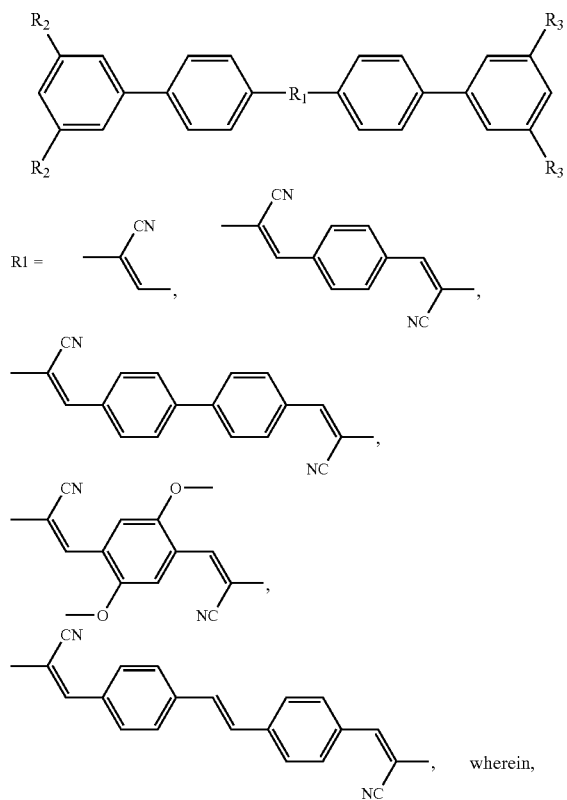

$R_2$ and $R_3$ denotes respectively $C_1$-$C_6$ alkyl, $C_1$-$C_6$ alkoxy, substituted or unsubstituted amino, or substituted or unsubstituted aryl, and the substituted or unsubstituted aryl can be condensed at the optional site of the corresponding two benzene rings.

2. An organic electro-luminescent composition comprising α-cyanostilbene compounds of the formula 1:

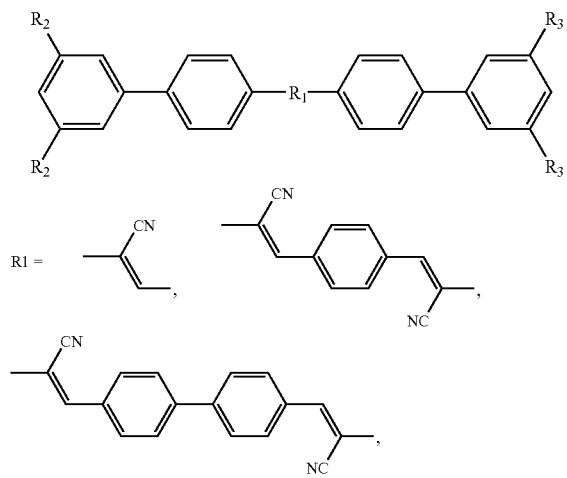
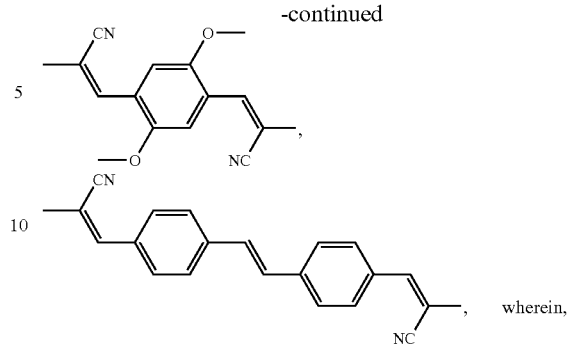

wherein, $R_2$ and $R_3$ denotes respectively $C_1$-$C_6$ alkyl, $C_1$-$C_6$ alkoxy, substituted or unsubstituted amino, or substituted or unsubstituted aryl, and the substituted or unsubstituted aryl can be condensed at the optional site of the corresponding two benzene rings.

3. An material in the state of powder, organic solution and film comprising α-cyanostilbene compounds of the formula 1:

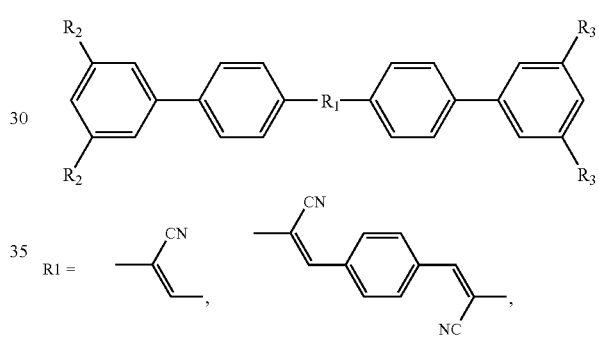
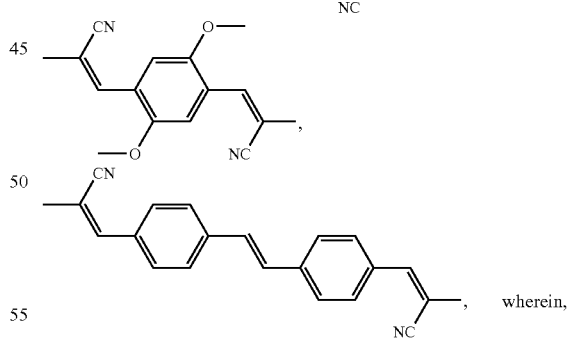

wherein, $R_2$ and $R_3$ denotes respectively $C_1$-$C_6$ alkyl, $C_1$-$C_6$ alkoxy, substituted or unsubstituted amino, or substituted or unsubstituted aryl, and the substituted or unsubstituted aryl can be condensed at the optional site of the corresponding two benzene rings.

* * * * *

UNITED STATES PATENT AND TRADEMARK OFFICE
CERTIFICATE OF CORRECTION

PATENT NO. : 7,592,475 B2  Page 1 of 1
APPLICATION NO. : 10/520291
DATED : September 22, 2009
INVENTOR(S) : Park et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1006 days.

Signed and Sealed this

Twenty-first Day of September, 2010

David J. Kappos
*Director of the United States Patent and Trademark Office*